(12) United States Patent
Farmer

(10) Patent No.: US 6,501,782 B1
(45) Date of Patent: Dec. 31, 2002

(54) COMPACT LASER APPARATUS

(75) Inventor: Jason N. Farmer, Kenmore, WA (US)

(73) Assignee: Aculight Corporation, Bothell, WA (US)

( * ) Notice: Subject to any disclaimer, the term of this patent is extended or adjusted under 35 U.S.C. 154(b) by 179 days.

(21) Appl. No.: 09/690,665

(22) Filed: Oct. 17, 2000

Related U.S. Application Data
(60) Provisional application No. 60/161,470, filed on Oct. 25, 1999.

(51) Int. Cl.[7] .................................................. H01S 3/08
(52) U.S. Cl. ........................ 372/92; 372/6; 372/98; 372/101; 372/102; 372/108; 385/129
(58) Field of Search .............................. 372/92, 6, 101, 372/98, 102, 108; 385/129, 10

(56) References Cited

U.S. PATENT DOCUMENTS

| | | | |
|---|---|---|---|
| 4,494,235 A | 1/1985 | Guch, Jr. et al. ............... 372/23 |
| 4,913,525 A | 4/1990 | Asakura et al. ......... 350/162.12 |
| 4,923,270 A | 5/1990 | Carter ...................... 350/96.18 |
| 5,007,698 A | 4/1991 | Sasaki et al. ............. 350/96.15 |
| 5,052,013 A | 9/1991 | Putnam ........................ 372/97 |
| 5,115,444 A | 5/1992 | Kirkby et al. ................. 372/50 |
| 5,136,420 A | 8/1992 | Inagaki et al. ............... 359/341 |
| 5,163,058 A | 11/1992 | Farries et al. .................. 372/6 |
| 5,276,695 A | 1/1994 | Scheps ........................ 372/20 |
| 5,351,262 A * | 9/1994 | Poguntke et al. ........... 372/102 |
| 5,386,426 A | 1/1995 | Stephens ..................... 372/20 |
| 5,390,201 A | 2/1995 | Tomono et al. ............... 372/22 |
| 5,450,232 A | 9/1995 | Sasaki et al. ................ 359/341 |
| 5,513,201 A | 4/1996 | Yamaguchi et al. .......... 372/75 |
| 5,541,946 A | 7/1996 | Scheps et al. ................ 372/23 |
| 5,773,345 A | 6/1998 | Ota .............................. 438/286 |
| 5,802,092 A | 9/1998 | Endriz .......................... 372/50 |
| 6,169,838 B1 * | 1/2001 | He et al. ..................... 385/129 |

FOREIGN PATENT DOCUMENTS

| EP | 0 440 485 A2 | 1/1991 | ............ G02B/6/34 |
|---|---|---|---|
| EP | 0793291 A2 * | 9/1997 | |

OTHER PUBLICATIONS

M.C. Farries et al., Electronics Letters, Aug. 15, 1991, vol. 27, No. 17, pp. 1498–1499.
J.B.D. Soole et al., Electronics Letters, Sep. 10, 1992, vol. 28, No. 19, pp. 1805–1807.
J.B.D. Soole et al., Appl. Phys. Lett. 61(23), Dec. 7, 1992, pp. 2750–2752.
J.B.D. Soole et al., Appl. Phys. Lett. 58(18), May 6, 1991, pp. 1949–1951.

* cited by examiner

Primary Examiner—Leon Scott, Jr.
(74) Attorney, Agent, or Firm—Bingham McCutchen LLP; David G. Beck

(57) ABSTRACT

An apparatus for combining the outputs from multiple gain elements of an array within a single resonator cavity to achieve a predetermined spectral output or improved output power is provided. The resonator cavity is comprised of a reflector, preferably deposited on the back facets of the gain element array, and an output coupler. Interposed between the gain element array and the output coupler are an optical element and a reflective diffraction grating. The optical element can be comprised of either a GRIN lens or a uniform index element with a shaped, reflectively coated back surface. The output coupler can be directly coupled to an optical fiber, for example by burying the output coupler into the entrance aperture of the fiber.

21 Claims, 1 Drawing Sheet

COMPACT LASER APPARATUS

CROSS-REFERENCES TO RELATED APPLICATIONS

This application claims priority of provisional patent application Ser. No. 60/161,470 filed Oct. 25, 1999, the disclosure of which is incorporated herein by reference for all purposes.

FIELD OF THE INVENTION

The present invention relates generally to optical systems and, more particularly, to an apparatus for combining the outputs from multiple gain elements of an array within a single resonator cavity.

BACKGROUND OF THE INVENTION

Semiconductor lasers utilizing GaAlAs, GaAs, InGaAs, and other materials have been developed that have found application in a variety of fields including telecommunications, medical testing/treatment, optical measurements, and optical disk reading/writing. Such lasers can be designed with either a single gain element or with an array of discrete gain elements. In order to utilize such lasers, it is often desirable to couple the output from several discrete gain elements into a single output beam, thereby achieving greater output power, spectral bandwidth, beam brightness, etc.

U.S. Pat. No. 5,802,092 discloses a diode laser source in which the output from each of a plurality of concurrently driven laser gain elements within a single diode array are passed through suitable beam filling and focusing optics in order to converge the outputs to a single overlapping spot. Each of the laser gain elements is individually addressable, thus allowing individual elements to fail with only a marginal effect on the optical power and brightness of the overlapping spot. As a result of this design, the lifetime of the device is improved.

U.S. Pat. No. 5,513,201 discloses a system designed to achieve an increased energy density at the light focus of a linear semiconductor laser array. The system utilizes an optical path rotating device interposed between a pair of collimating elements. Each of the collimating elements is designed to provide collimation along a single axis. The system also includes a focussing element for condensing the laser beams that have been collimated in both directions.

U.S. Pat. No. 4,494,235 discloses a frequency stabilized semiconductor laser which utilizes a Fourier diffraction grating with a corrugation having continuous first order differential coefficients. In operation, the semiconductor laser emits a beam from one facet into the diffraction grating. The diffracted light from the grating is fed back into the semiconductor laser in such a way as to cause the semiconductor to emit an output beam with a stable wavelength from another facet. The grating can be rotated to achieve different wavelengths.

U.S. Pat. No. 5,276,695 discloses a tunable, optically pumped, solid state laser which simultaneously emits light at one or more wavelengths. The resonator uses two or more end reflective elements, two curved fold mirrors, and an output coupler reflective element. A wavelength dispersive element, e.g., a prism, is disposed in the reflective path in the laser resonator cavity between one fold mirror and the end reflective element, the wavelength dispersive element providing wavelength tuning capability. In order to optimize the wavelength dispersion performance of the dispersive element, the laser cavity mode is collimated as it passes through the element.

U.S. Pat. No. 5,541,946 discloses a laser which simultaneously emits light at two or more wavelengths. The laser includes at least two gain elements pumped by a single optical pumping source, each gain element generating a different wavelength. The resonator uses two plane highly reflective end elements, three concave fold elements, and an output coupler. A wavelength dispersive element, e.g., a prism, is disposed in the reflective path in the laser resonator cavity to provide a spatially separate path for each of the simultaneously emitted wavelengths. In order to optimize the wavelength dispersion performance of the dispersive element, the laser cavity mode is collimated as it passes through the element.

A tunable semiconductor laser with a single output is disclosed by Soole et al. in *Wavelength-selectable Laser Emission from a Multistripe Array Grating Integrated Cavity Laser*, Applied Physics Letters 61 (23), Dec. 7, 1992. In the disclosed system, an array of active laser elements is optically coupled to a fixed, etched-in, diffraction grating. Wavelength tuning is accomplished through selective activation of individual laser elements, the wavelength being determined by the position of the activated laser element relative to the etched-in grating.

Although a variety of intracavity beam combiners have been designed, these devices typically require very precise alignment. Accordingly, what is needed in the art is a robust intracavity beam combining system utilizing multiple discrete gain elements and a resonator structure that is primarily contained within a single optical element, thus minimizing system alignment requirements. The present invention provides such a device.

SUMMARY OF THE INVENTION

The present invention provides an apparatus for combining the outputs from multiple gain elements of an array within a single resonator cavity using a diffraction grating. The apparatus can be used to achieve a predetermined spectral output or to achieve a relatively high output power from an array of low power laser elements. The multiple gain element array can be a semiconductor diode laser array, an array of side or end pumped solid state laser materials, or a fiber laser array.

In at least one embodiment of the invention, the resonator cavity is comprised of a reflector, preferably deposited on the back facets of the gain element array, and an output coupler. Interposed between the gain element array and the output coupler is an approximately ¼ pitch GRIN lens and a reflective diffraction grating, the reflective diffraction grating coupled to the back surface of the GRIN lens. The output coupler is preferably coupled to an optical fiber.

In at least one other embodiment of the invention, interposed between the gain element array and the output coupler of the resonator cavity is an optical element in which the back surface is shaped and onto which a highly reflective coating is deposited. Coupled to the front surface of the optical element is a diffraction grating. An entrance aperture on the front surface of the optical element allows light from the gain element array to enter the optic. The light from each element of the array is reflected off of the back surface of the optic onto the diffraction grating, reflected by the diffraction grating back towards the back surface of the optic, and focused by the back surface of the optic onto the output coupler.

A further understanding of the nature and advantages of the present invention may be realized by reference to the remaining portions of the specification and the drawings.

DESCRIPTION OF THE SPECIFIC EMBODIMENTS

Figure 1:
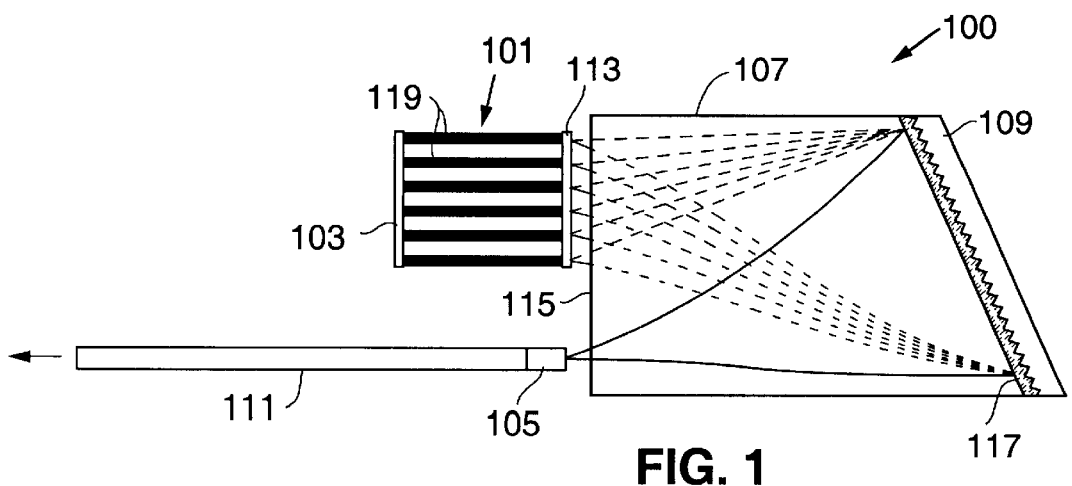
FIG. 1 is an illustration of a laser system fabricated in accordance with the invention utilizing a GRIN lens.

FIG. 1 illustrates a laser system 100 in accordance with the invention. Laser system 100 includes a laser gain element array 101 that is coupled to an external resonator cavity comprised of a high reflectance coating 103 applied to the back facets of array 101 and an output coupler 105. Interposed between array 101 and output coupler 105 is a gradient index or GRIN lens 107 and a reflective diffraction grating 109.

In the preferred embodiment of the invention, output coupler 105 is directly coupled to an optical fiber 111, preferably a single mode fiber. Output coupler 105 can be buried within fiber 111, attached to fiber 111 with an index matching, optically transparent adhesive, or directly deposited onto the cleaved end facet of fiber 111. Preferably the optical losses in system 100 are minimized through the application of an anti-reflection or AR coating to facets 113 of array 101 and end face 115 of GRIN lens 107, the AR coating being designed for the wavelength or wavelengths of interest using known coating design techniques.

GRIN lens 107 is approximately a ¼ pitch GRIN lens with diffraction grating 109 bonded to an end face 117 of lens 107 using an index matching, optically transparent adhesive. Alternately, diffraction grating 109 can be fabricated directly onto surface 117 of GRIN lens 107 using any of a variety of known techniques.

As a result of the combination of GRIN lens 107 and reflective diffraction grating 109, each gain element 119 of array 101 oscillates within its own cavity, the wavelength of which is defined by the diffraction grating. Additionally, the combination of GRIN lens 107 and diffraction grating 109 allows each resonant cavity to utilize the same output coupler, i.e., output coupler 105, and hence each resonant cavity shares the same output beam path. Thus the present invention can be used to produce a relatively high output power from an array of low power laser elements, the apparatus output being within a relatively narrow wavelength band. Alternately, each element 119 of array 101 can form a resonant cavity oscillating within a different wavelength band, thus yielding a multispectral laser apparatus. If desired, the present invention can be used to couple the relatively high power from an array of low power laser elements into a single mode fiber.

Figure 2:
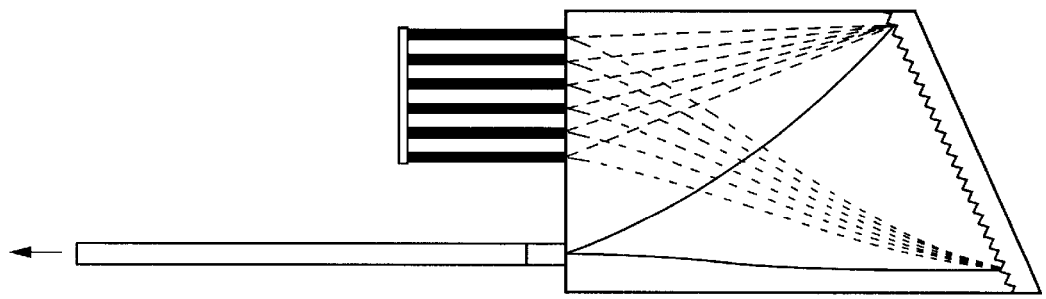
FIG. 2 is an illustration of a compact, robust configuration of the system illustrated in FIG. 1.

In order to provide a more robust laser system, array 101 can be bonded directly to end face 115 of GRIN lens 107 as shown in FIG. 2. Similarly, output coupler 105 can be bonded directly to end face 115 of GRIN lens 107 as shown.

As a result of the resonator structure being primarily contained within the GRIN lens, a laser system fabricated in accordance with the present invention is less sensitive to alignment errors than a conventional intracavity beam combining apparatus. The principal source of alignment in a laser system fabricated in accordance with the present invention is the angular alignment of the output coupler.

Active elements 119 can either be single mode or multimode gain elements, depending upon the desired application. In the preferred embodiment of the invention, array 101 is a semiconductor diode laser array. Other gain elements, however, can be used. For example, the gain elements can be side or end pumped solid state laser materials which are stacked together. Suitable solid state laser materials include, but are not limited to, Nd:YAG, Nd:YLF, Nd:YVO$_4$, and Cr:LiSAF. Alternately, array 101 can be comprised of an array of fiber lasers.

Figure 3:
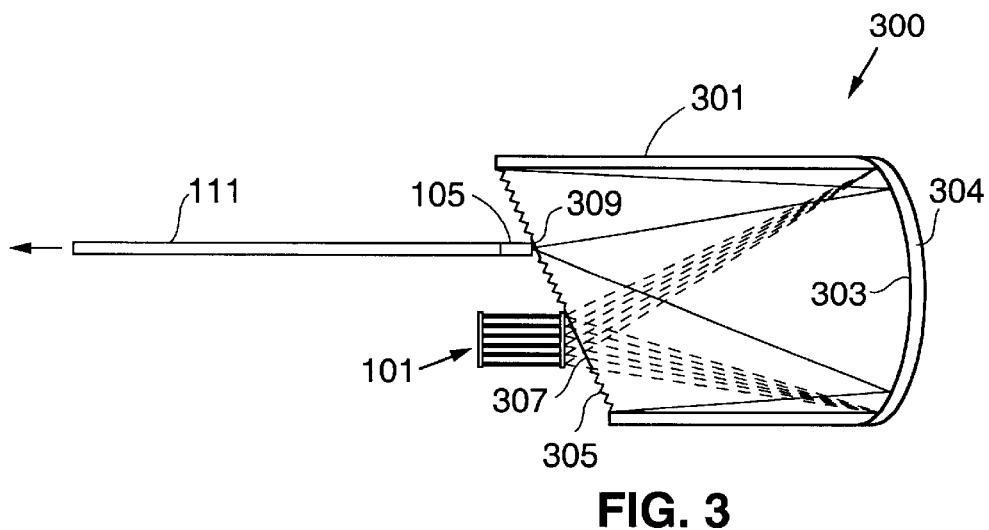
FIG. 3 is an illustration of an alternate embodiment of the invention.

FIG. 3 is an illustration of an alternate embodiment of the invention. As in the previously illustrated embodiment, system 300 is designed to utilize single output coupler 105 for each element 119 of an array 101 of gain elements. Preferably output coupler 105 is coupled to single mode fiber 111, for example by burying the output coupler into the entrance aperture of the fiber. However, as opposed to GRIN lens 107, system 300 uses a single optic 301 of uniform index. A shaped back surface 303 of optic 301 is coated with a highly reflective optical coating 304, preferably designed for the wavelength or wavelengths emitted by array 101. In this embodiment a reflective diffraction grating 305 is coupled to the front surface of optic 301, grating 305 including an entrance aperture 307 for array 101 and an output aperture 309 for output coupler 105. Preferably output coupler 105 is deposited directly onto the front surface of optic 301 at aperture 309 and fiber 111 is coupled, for example using an index matching adhesive, to aperture 309 and thus coupler 105. Preferably the front facets of array elements 119 and entrance aperture 307 are AR coated to minimize optical losses. More preferably, array 101 is bonded directly to entrance aperture 307, thus providing an extremely robust optical system.

As illustrated in FIG. 3, reflector 304 on curved surface 303 first directs the light from each array element 119 onto reflective grating 305, and then focuses the light diffracted by grating 305 onto output coupler 105. Preferably the light from array elements 119 is substantially collimated by reflective surface 304 onto the diffraction grating.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A laser resonator cavity comprising:
   a laser gain element array comprised of a plurality of laser gain elements;
   a GRIN lens, wherein emissions from said plurality of laser gain elements pass through said GRIN lens;
   a reflective diffraction grating, wherein emissions passing through said GRIN lens from said plurality of laser gain elements spatially overlap on said diffraction grating and are diffracted by said diffraction grating back through said GRIN lens; and
   an output coupler, wherein emissions from said plurality of laser gain elements reflected by said diffraction grating are focused onto said output coupler.

2. The laser resonator cavity of claim 1, wherein said GRIN lens is a substantially ¼ pitch GRIN lens.

3. The laser resonator cavity of claim 1, wherein said reflective diffraction grating is bonded to said GRIN lens with an index matching adhesive.

4. The laser resonator cavity of claim 1, wherein said reflective diffraction grating is etched into said GRIN lens.

5. The laser resonator cavity of claim 1, further comprising a reflector proximate to a rear facet of each of said plurality of laser gain elements.

6. The laser resonator cavity of claim 5, wherein said reflector is deposited on said rear facet of each of said plurality of laser gain elements.

7. The laser resonator cavity of claim 1, wherein said laser gain element array is selected from the group of arrays consisting of semiconductor diode laser arrays, side pumped solid state laser materials, end pumped solid state laser materials, and fiber laser arrays.

8. The laser resonator cavity of claim 1, further comprising an anti-reflection coating deposited on a front facet of each of said plurality of laser gain elements.

9. The laser resonator cavity of claim 1, further comprising an optical fiber coupled to said output coupler.

10. The laser resonator cavity of claim 9, wherein said optical fiber is a single mode fiber.

11. The laser resonator cavity of claim 9, wherein said output coupler is buried within an entrance aperture of said optical fiber.

12. A laser resonator cavity comprising:

a laser gain element array comprised of a plurality of laser gain elements;

an optical element of a uniform optical index, wherein emissions from said plurality of laser gain elements pass through an entrance aperture on a leading surface of said optical element;

a reflective coating coupled to a shaped back surface of said optical element, wherein said reflective coating on said shaped back surface substantially collimates said emissions from said plurality of laser gain elements;

a reflective diffraction grating coupled to said leading surface of said optical element, wherein said substantially collimated emissions from said plurality of laser gain elements are reflected by said diffraction grating back through said optical element, wherein said reflective coating on said shaped back surface substantially focuses said emissions from said plurality of laser gain elements reflected by said diffraction grating, wherein said focussed emissions pass through an exit aperture on said leading surface of said optical element; and an output coupler proximate to said exit aperture, wherein emissions from said plurality of laser gain elements focussed by said reflective coating on said shaped back surface are focused onto said output coupler.

13. The laser resonator cavity of claim 12, wherein said laser gain element array is bonded to said entrance aperture of said leading surface of said optical element with an index matching adhesive.

14. The laser resonator cavity of claim 12, wherein said output coupler is bonded to said exit aperture of said leading surface of said optical element with an index matching adhesive.

15. The laser resonator cavity of claim 12, further comprising a reflector proximate to a rear facet of each of said plurality of laser gain elements.

16. The laser resonator cavity of claim 15, wherein said reflector is deposited on said rear facet of each of said plurality of laser gain elements.

17. The laser resonator cavity of claim 12, wherein said laser gain element array is selected from the group of arrays consisting of semiconductor diode laser arrays, side pumped solid state laser materials, end pumped solid state laser materials, and fiber laser arrays.

18. The laser resonator cavity of claim 12, further comprising an anti-reflection coating deposited on a front facet of each of said plurality of laser gain elements.

19. The laser resonator cavity of claim 12, further comprising an optical fiber coupled to said output coupler.

20. The laser resonator cavity of claim 19, wherein said optical fiber is a single mode fiber.

21. The laser resonator cavity of claim 19, wherein said output coupler is buried within an entrance aperture of said optical fiber.

* * * * *